United States Patent [19]

Snyder

[11] 4,311,685
[45] * Jan. 19, 1982

[54] ASSAY METHOD AND KIT

[75] Inventor: Solomon H. Snyder, Baltimore, Md.

[73] Assignee: Burroughs Wellcome Co., Research Triangle Park, N.C.

[*] Notice: The portion of the term of this patent subsequent to Feb. 3, 1998, has been disclaimed.

[21] Appl. No.: 49,418

[22] Filed: Jun. 18, 1979

Related U.S. Application Data

[63] Continuation-in-part of Ser. No. 940,712, Sep. 8, 1978, Pat. No. 4,248,853.

[51] Int. Cl.³ .................. G01N 33/60; G01T 1/00
[52] U.S. Cl. .................................... 424/1; 23/230 B; 424/12
[58] Field of Search .................. 424/1, 12; 23/230 B; 422/67

[56] References Cited

U.S. PATENT DOCUMENTS 4,026,879  5/1977  Spector .................................. 424/1
4,070,492  1/1978  Spector .................................. 424/1

OTHER PUBLICATIONS

Innis et al., Life Sciences, vol. 23 (1978) pp. 2031–2038.
Snyder et al., Nature, vol. 270 (Nov. 1977) pp. 261–263.
Nahorski et al., Eur. J. Pharma, 52 (1979) pp. 393–396.
Bilezikian et al., Clin. Pharmacol. Ther., vol. 26, No. 2 (1979) pp. 173–180.

Primary Examiner—Christine M. Nucker
Attorney, Agent, or Firm—Donald Brown

[57] ABSTRACT

Method and materials for determining levels of β-adrenergic blocking drugs in body fluid, the method including the step of measuring inhibition of the binding of β-adrenergic receptor binder to β-adrenergic receptor material caused by β-adrenergic blocker present in the body fluid.

19 Claims, 1 Drawing Figure

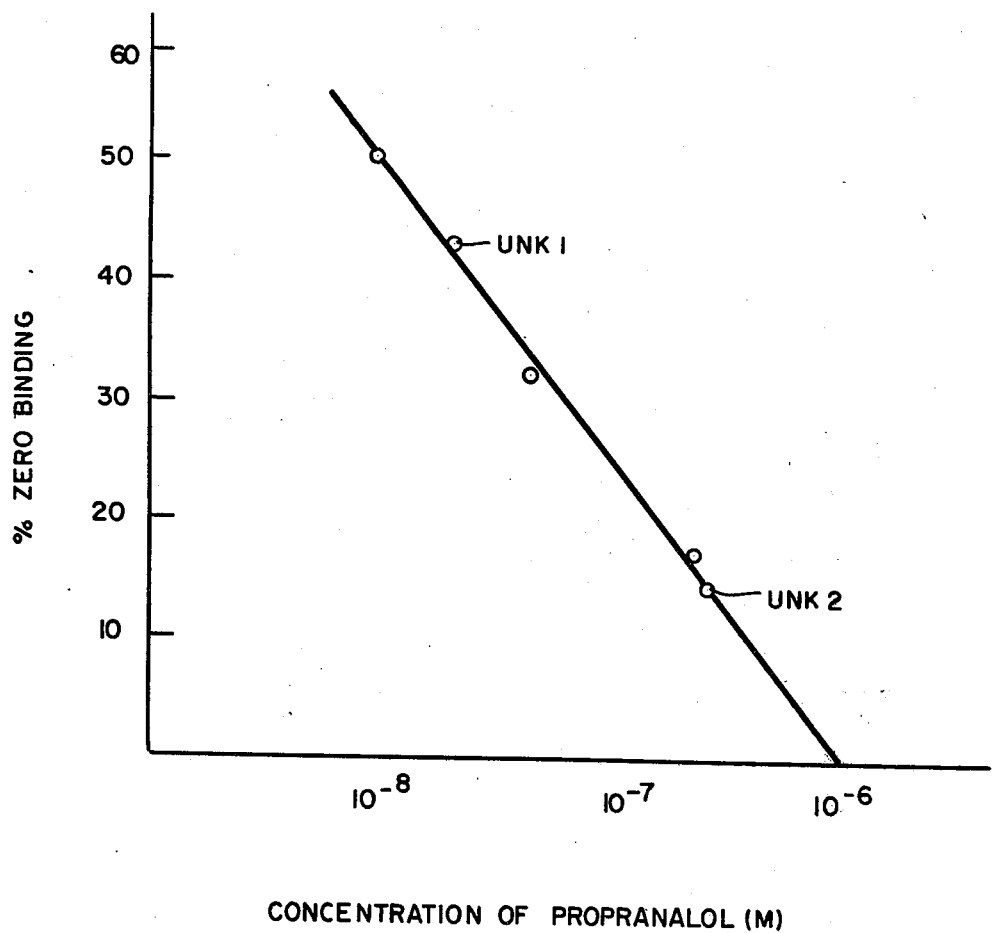

ASSAY METHOD AND KIT

PRIOR APPLICATION

This application is a continuation-in-part of Ser. No. 940,712 filed Sept. 8, 1978, now U.S. Pat. No. 4,248,853.

BACKGROUND OF THE DISCLOSURE

Drugs which can block β-adrenergic receptors are among the most valuable agents used presently in clinical medicine. In the United States the major drug employed clinically is propranolol, while numerous other agents are available commercially in Europe and probably will be used in the United States within the next few years. These drugs are used extensively throughout the world for the treatment of hypertension and angina pectoris. Dosage requirements can vary considerably among different patients. In part the variable dose requirement is related to differences in absorption and metabolism of the drug among individuals. Attaining the optimal dose is important in securing maximal therapeutic benefit and in avoiding potentially serious side effects of these drugs such as abnormalities in cardiac rhythm and blood pressure. It is generally felt that a simple and sensitive technique to measure these drugs in blood and other body tissues would facilitate the selection of optimal doses.

Detecting β-adrenergic blocking drug levels in body fluids ideally should employ a technique which can be used with all of the agents. Moreover, it has been established with propranolol that a metabolite of the drug 4-hydroxypropranolol has therapeutic activity so that an ideal method should be able to measure pharmacologically active but not inactive metabolites in addition to the parent drug.

Presently available techniques include gas-liquid chromatography, fluorimetric procedures as well as radio-immunoassays. None of these have attained routine clinical use because of various technical problems. Most of these techniques are applicable for individual drugs rather than for the whole class of β-blocking agents. Also such prior art methods do not specifically detect active metabolites.

β-adrenergic blocking drugs were developed on the basis of their ability to antagonize the effects of adrenergic stimulating substances such as the natural neurotransmitter, norepinephrine or its analogue, isoproterenol, which has a uniquely high potency in stimulating β-adrenergic receptors. In recent years it has been possible to label β-adrenergic receptors in a variety of tissues using radioactive β-blocking drugs (binder) such as $^3$H-dihydroalprenolol and $^{125}$I-hydroxybenzylpindolol. See the publications Lefkowitz et al, Biochem. Biophys, Res. Commun. 60:703-709, 1974; Aurbach et al, Science, 186:1223-1224, 1974. Neither of these publications nor any of several publications appearing in the succeeding years describing the binding of these and other radioactive drugs to the β-receptor have disclosed anything beyond the fact that β-adrenergic receptors can be measured with various radioactive forms of β-blocking drugs, that β-blocking drugs compete with the binding of these radioactive agents for the receptor, and that β-adrenergic cardiac blockage is believed to be more closely correlated with free drug levels in the blood rather than total plasma blood levels. See McDevitt et al, Clin. Pharmacol. There, 20:152-157, 1976.

Moreover, the information contained in these above-mentioned publications does not provide a tool for measuring amounts of β-blocking drugs in body fluids of human patients, because a number of needed elements, all of which were yet to be discovered, had to be discovered to exist for a successful assay for levels of β-blocking drugs. For a successful assay for β-blocking drug levels it was necessary to discover the nonspecific effects of body fluids on the binding properties of the β-receptors and discover means of reducing or abolishing them. It was also necessary to discover that β-blocking drugs added to body fluids could be recovered in a form that would still interact with the β-adrenergic receptors. It was also necessary to show that in the presence of body fluids increasing amounts of β-blocking drugs would in a predictable fashion produce progressively greater blockage of β-receptors. Only after making a series of discoveries as disclosed herein which reduced nonspecific effects of body fluids on the β-receptors, permitted recovery of added β-blocking drugs and resulted in reproducible augmentations in receptor blockage with increasing amounts of β-blocking drugs in body fluids was it possible to measure β-blocking drugs and active metabolites in body fluids with this invention.

BRIEF DESCRIPTION OF THE DISCLOSURE

The present invention is directed to a new technique which permits rapid determination of the concentration of β-adrenergic blocking drugs in patients. The making of this determination was important in order to obtain the desired medical effect of these drugs. While the desirable concentration of β-adrenergic blocking drug in the patient's blood or other bodily fluids is known, it has been found that the uptake of these drugs by most patients is variable so that one has no assurance that a certain dose of β-adrenergic blocking drug administered to the patient will produce the desired concentration in the blood. The prior techniques for measuring the concentrations of β-blocking drugs, as mentioned previously, are not applicable to all available β-adrenergic blocking drugs and do not detect active but not inactive metablolites. Accordingly, a new and improved technique that could easily and rapidly be used was needed to insure that patients were being properly dosed to achieve beneficial effects without causing harmful side effects.

The present invention provides such a technique and is based on the fact that β-adrenergic blocking drugs will successfully compete with the binding of radioactive β-blocking drugs to β-adrenergic receptors in such a manner that an accurate determination of β-adrenergic blocking drug concentration can readily be determined.

The present invention is also based in part upon the discovery that once the competition of radioactive β-adrenergic blocking drug to β-adrenergic receptor has proceeded for the desired time, labeled drug and receptor can be successfully separated from free drug and receptor and bodily fluids without destroying the accuracy of the concentration measurement to be made. It has also been found that effective drug levels in blood plasma can be measured even more accurately if a means of eliminating or diminishing the effect of the binding of β-adrenergic drug to plasma proteins is included in the technique prior to the competition step.

After the separation, the level of radioactive β-blocking drug may be measured in a conventional radioactive measurement device, e.g. scintillation counter or gamma counter depending on the radionuclide of the radioactive β-adrenergic blocking drug and compared with standard curves to determine the concentration of the β-adrenergic blocking drug in the patient.

Thus, there is described herein a method for measuring levels of β-blocking drugs, including levels of free drugs and active metabolites thereof, in patients based on the ability of these drugs to compete with the binding of radioactive β-blocking drugs (ligands) including β-adrenergic antagonists or agonists to β-adrenergic receptors in β-adrenergic receptor containing material. An active metabolite is a compound which itself acts as a β-blocking drug and is somehow formed in the patient (human) body from the drug (directly or indirectly).

In this procedure increasing amounts of β-adrenergic blocking drugs or active metabolites thereof decrease the binding of the radioactive labeled binder to the β-adrenergic receptor material. The biological fluid sample may be assayed without separation of the β-adrenergic blocking drug therefrom, e.g. blood serum or blood plasma may be directly assayed to determine the β-blocking drug level, although it is preferred that plasma dialysates be used for assay of blood plasma, since plasma protein inhibits the binding of radioactive binder to β-adrenergic receptor material when present in more than minimal amounts. Other methods for separating free from protein bound drug can also be used in conjunction with the assay.

Suitable β-adrenergic receptor material is obtained from animal tissues enriched in these receptors such as the brain, heart, lung, and blood cells. Suitable receptor material is obtained from humans or from animal species such as bovine, rodent (rat) or birds.

The β-adrenergic receptor material may be used as such or fractionated in a conventional manner to obtain fractions enriched in receptor-containing membranes and may be washed or unwashed.

The β-adrenergic receptor material may preferably be sold as a conventional freeze-dried preparation in a test tube, e.g. coupled to the interior of a test tube so that the binder and drug may be easily added to it.

As the radioactive β-adrenergic receptor binder, radioactive labeled compounds such as $^3$H-dihydroalprenolol, $^{125}$I-Hydroxybenzylpindolol, $^3$H-epinephrine or any other analogues of norepinephrine or of β-adrenergic blocking drugs having the β-adrenergic receptor binding properties exhibited by these compounds may be used.

In principal, these compounds are conventionally labeled in the manner well known in the prior art with any radionuclide. A listing of the radionuclides which are now conventionally in use in reagents and which may be used in this invention are listed in the index of radionuclides found on page 81 of the 1978 edition of the Catalogue of the New England Nuclear Corporation, Boston, Mass., U.S.A. (New England Nuclear, 1977). Among radionuclides which are preferred in this invention the following may be mentioned; hydrogen-3(tritium) and the radio isotopes of iodine ($^{123}$I, $^{124}$I, $^{125}$I, $^{126}$I, $^{128}$I, $^{130}$I and $^{132}$I) with $^{125}$I and $^{131}$I being preferred from considerations of availability, half life and specific activity and the ability of radioactive iodine compounds to be readily labeled using a conventional gamma counter usually available in hospitals and sold by Packard Instruments or others.

In a typical experiment the membranes (β-adrenergic receptor material) can be incubated at various temperatures for various periods of time with appropriate ligand (β-adrenergic receptor binder). Typically $^3$H-dihydroalprenolol or $^{125}$I-hydroxybenzylpindolol of high specific radioactivity purchased from New England Nuclear of Boston, Mass. is incubated with rat or calf brain membranes in a buffer solution at a pH of 7.7 at a temperature of 37° for 30 min. and then filtered under vacuum through Whatman GF/B filters with two 5 ml. rinses of cold buffer. The filters can be counted in liquid scintillation counters, e.g. Packard Instrument scintillation spectrometer model 3385. Counting may also be accomplished using a gamma counter.

Specific binding to the β-adrenergic receptor is determined as the excess over blanks taken in the presence of 10 μM norepinephrine or 0.1 μM propranolol though blank values can be obtained using a variety of other agents that bind to the β-adrenergic receptor. The ligand can be any β-adrenergic agonist or antagonist or mixed agonist-antagonist labeled with radioactivity.

Biological fluid samples, e.g. urine, blood plasma, blood serum, etc., supposedly containing β-adrenergic blocking drugs are added to this assay. The biological samples can be added without any purification or may be subjected to purification procedures. Purification or concentration of the biological fluid containing the β-blocking drugs can employ any of numerous chemical techniques including solvent extraction, column chromatography, adsorption onto specially treated fibers or other chemical substance or by any other chemical procedure which may help purify the β-blocking drug or concentrate. When the biological fluid sample contains blood plasma, the sample is preferably dialysed against a suitable buffer in a suitable dialysis apparatus, e.g. Krebs-Ringer solution in a Hoefer Scientific EMD dialysis apparatus. An alternative procedure is to dilute the sample with buffer until a 1 ml assay sample contains about 1 μl or 2 μl of plasma although this may make detection difficult in some patients. The amount of β-adrenergic blocking drug is quantified by the extent to which it decreases binding of the labeled ligand to the β-adrenergic receptor. The values can be qualified in any convenient units. The incubation mixture for the receptor binding can include any of numerous additives to facilitate binding or to protect the drugs or labeled ligands. The duration of the incubation and its temperature can vary and involve any convenient period, though it is usually best to conduct the incubation to equilibrium, e.g. suitable time for incubation could be anywhere from two min. to 4 hrs., 30 min. being preferred. Receptor bound ligand can be trapped by filtration, centrifugation or any other known techniques which separate bound from unbound ligand.

It should also be understood that other suitable trapping techniques may also be used so long as it will permit the retention of the large sized β-adrenergic receptor material having bound radioactive binder and β-adrenergic blocking drug while being able to separate the unbound radioactive binder (ligand) and free β-adrenergic blocking drug. Other examples of suitable filter material include Millipore filters of various sizes, e.g. 0.6 micron diameter holes.

Preferably the β-adrenergic receptor material is buffered by a buffering solution such as Tris-HCl buffer sold by Sigma Labs, St. Louis, Mo., having a pH of 7.7. Other suitable buffering solutions include sodium phosphate buffer, glycine buffer and Hepes buffer and others which will provide the preferred pH (6–9) in the mixture to permit rapid binding of the radioactive labeled binder to the β-adrenergic receptor material.

Thus this invention provides a new and improved method for determining concentration in humans of β-adrenergic blocking drugs such as propranolol, practolol, pindolol, alprenolol, sotalol, butoxamine, and others which are known in the art as competitors at β-adrenergic receptors.

In particular, the method is easily practiced by preparing a mixture of radioactive binder, body fluid, e.g. blood serum, blood plasma or urine and β-adrenergic receptor material, measuring the radioactivity (counts) of the binder attached to the β-adrenergic receptor material preferably after separating unbound materials, (e.g. blood serum or plasma, binder drug if present, etc.) from the β-adrenergic receptor material and then deriving the concentration of the β-adrenergic blocking drug from a standard curve which indicates the concentration of β-blocking drug versus inhibition of the radioactive binder binding to the β-adrenergic receptor material caused by the β-adrenergic blocking drug in the blood serum or plasma.

It has been discovered that the concentrations of body fluids in the assay are most preferably no greater than about 10% of the total assay volume of ingredients in the test tube, preferably no more than 1.0% if blood plasma is the body fluid. Concentrations of plasma in excess of 1.0% or serum in excess of about 1.0% inhibit markedly binding of $^3$H-ligands to the β-adrenergic receptor even without any drug present. Optimally the concentration values should be less than 1.0%. Concentrations in excess of 1.0% may affect the validity of the assay test results. In this method the amount of body fluid is preferably greater than one microliter to assure consistently good results. As used herein the total assay volume ingredients means the sum of ingredients in the test tube and the like prior to washing and adding scintillation fluid.

In addition, this invention provides a new composition of matter concerning radioactive binder, β-adrenergic blocking drug and β-adrenergic receptor material and blood serum or plasma and a kit as a merchantile unit comprising at least one container containing the following ingredients: β-adrenergic receptor material, radioactive receptor binder for these receptor materials, and a standard amount of non-radioactive receptor binder. Each of these ingredients may also be packaged in one or more individual containers.

BRIEF DESCRIPTION OF THE DRAWINGS

FIG. 1 herein is a graph showing percent zero binding vs propranalol in molar concentration reported in Example I.

EXAMPLE I

The following example illustrates measurement of blood serum propranalol levels:
Materials
I. β-adrenergic receptor:

Cerebellar membranes were used as a source for β-adrenergic receptors. Three rats were decapitated. Their cerebellum, which had a combined weight of 0.72 g, was immediately dissected and homogenized in 10 ml. of ice-cold 500 mM Tris.HCl buffer, pH 7.7 with a Brinkman polytron (setting 3.7) for two minutes. Twenty milliliters of the Tris buffer was then added to the homogenate and the homogenate was centrifuged at 4° C. for 10 minutes at 40,000×g in a Sorval RC5 centrifuge. The pellet was homogenized in 10 ml. of the ice-cold Tris buffer with a polytron as previously described. Twenty milliliters of the ice-cold Tris buffer were added and the homogenized pellet was centrifuged at 40,000×g for 10 minutes. The pellet was again homogenized as previously described in 100 ml. of ice-cold 50 mM HCl, pH 7.7 and adjusted to a final volume of 30 ml. by adding 20 ml. of ice-cold 50 μM Tris HCl pH 7.7

II. Propranolol standards:

Six propranolol standards were prepared by dissolving varying concentrations of d,l-propranolol in pooled human serum as follows:
A. $10^{-4}$ M propranolol in human serum.
B. Human serum with no added propranolol.
C. $10^{-6}$ M propranolol in human serum.
D. $2\times10^{-7}$ M propranolol in human serum.
E. $4\times10^{-8}$ M propranolol in human serum.
F. $8\times10^{-9}$ M propranolol in human serum.
As used herein human serum means human blood serum.

III. Unknown:

Patients' serum or d,l-propranolol dissolved in human serum.

IV. Labeled ligand:

l[propyl-2,3-$^3$H]dihydroalprenalol (30 Ci/m mol), obtained from the Radiochemical Centre, Amersham, was diluted in 50 mM Tris.HCl pH 7.7 to give 10,000 CPM per 20 μl.

V. Assay procedure:

The assay is performed in 12×75 mm glass test tubes. Standard and unknown samples are assayed in triplicate. To each tube the following additions are made in order while the tubes are kept on ice: Twenty microliters of propranolol standard or 20 μl of unknown, twenty microliters of labeled ligand, one milliliter of β-adrenergic receptor cerebellar membranes. The tubes are then mixed with a vortex mixer and incubated at room temperature for 30 minutes. After this incubation the contents of tubes are each rapidly filtered with suction through Whatman GF/B glass fiber filters which have been placed in a filter manifold. The filters are rapidly washed twice with 5 ml. of ice-cold 50 mM Tris HCl pH 7.7. The filters are then placed in 12 ml. of Aquasol in 20 ml. liquid scintillation vials. After 16 hours the filters are counted for 2 minutes in a liquid scintillation counter using a $^3$H window setting (Packard Spectrometer).

VI. Calculation of results:

The average counts per minute for each set of triplicates is obtained. The average minus background counts per minute is obtained by subtracting the average counts per minute for standard A from the average counts per minute for each other set of standards and unknowns. The % zero binding is obtained by dividing the average minus the background counts per minute for each set of standards and unknowns by the average minus the background counts per minute for standard B and multiplying the result by 100. The % zero binding for the standards are then plotted against the log 10 of the concentration of propranolol in each standard. The log 10 of concentration of propranolol in the unknown is then determined by reading of the % zero binding for each unknown. The anti-logarithm then will give the concentration of propranolol in the unknown sample.

EXAMPLE

| Sample | Ave. CPM | Ave-BKG CPM | % Zero binding |
|---|---|---|---|
| Standard A | 789 | | |
| Standard B | 1574 | 785 | |
| Standard C | 619 | <0 | <0 |
| Standard D | 937 | 148 | 18.9 |
| Standard E | 1047 | 258 | 32.9 |
| Standard F | 1186 | 397 | 50.6 |
| Unk1($2 \times 10^{-7}$M proran) | 911 | 122 | 15.5 |
| Unk2($10^{-8}$M propran) | 1128 | 339 | 43.2 |

See the drawing (graph) which illustrates a plot of the data in the example and shows the concentration of propranolol of the unknown 1 and 2 in terms of molar concentration.

EXAMPLE II

The following example illustrates measurement of free levels of propranolol in blood serum.

Materials:

I. β-adrenergic receptor:

The radioreceptor assay used frozen calf cerebellum as a source of membrane bound β-receptor. The tissue was thawed in Krebs-Ringer buffer and then homogenized in 20 volumes of ice-cold 50 mM Tris/HCl pH 7.7 at 25° C. with a Brinkman Polytron PT 10 (setting 6, 30 sec). The homogenates were centrifuged twice at 50,000×g for 10 min. With an intermediate rehomogenization in fresh buffer. The final pellet was resuspended in 250 volumes ice-cold 50 mM Tris/HCl.

II. Unknown:

Human blood plasma from nine human subjects designated A-I and the sample from each subject being divided into two portions and triplicate samples prepared containing $7 \times 10^{-8}$ (±)—propranolol or no propranolol is incubated and dialyzed against 1 ml Krebs-Ringer solution in an EMD dialysis apparatus (Hoefer Scientific). Equilibrium is achieved by 12 hrs.

III. Labelled ligand:

(−) −[$^3$H]Dihydroalprenolol (58.6 Ci/mmole), obtained from New England Nuclear, Boston, Mass., is used as received.

IV. Assay procedure:

To triplicate incubation tubes were added 150 μl dialysate, 830 μl freshly resuspended tissue (about 3.3 mg of original tissue weight), and 20 μl (−)—[$^3$H]-Dihydroalprenolol (58.6 Ci/mmole, New England Nuclear) to give a final concentration of 0.5 nM. Tubes were incubated at 23° C. for 20 min and then filtered rapidly under vacuum through Whatman GF/B filters. The filters were rinsed three times with 5 ml ice-cold buffer and subsequently counted by liquid scintillation spectrometry in 10 ml Formula 947 (New England Nuclear). Specific binding of $^3$H-DHA was defined as the excess over blanks containing 0.2 μM (±)—propranolol. For the standard curve of displacement by (±)—propranolol, instead of 150 μl of dialysate, 10 μl of solutions of (±)—propranolol and 140 μl Krebs-Ringer were added to the assay tubes. The standard curve was plotted on log probigraph paper as described in Example I.

V. Calculation of results:

Taking into account the 6.7 fold dilution in the assay tubes, the concentration of propranolol in the dialysate was determined from the standard displacement curve as described in Example I. The % free propranolol was calculated as:

$$\% \text{ free} = \frac{\text{dialysate (Propranolol)}}{\text{original plasma (Propranolol)} - \text{dialysate (Propranolol)}}$$

Similarly, for $^3$H-propranolol:

$$\% \text{ free} = \frac{\text{dialysate cpm/ml}}{\text{original plasma cpm/ml} - \text{dialysate cpm/ml}}$$

The percent free propranolol when determined by radioreceptor assay was compared with a determination given by quantifying $^3$H propranolol, the result being given in the following table:

Free Propranolol Levels in Human Plasma

| Sample | [Propranolol] in dialysate $^+$(M) | %Free | CPM $^3$H-propranolol* | %Free |
|---|---|---|---|---|
| A | $5.2 \times 10^{-9}$ | 8.1 | 2287 | 9.5 |
| B | $8.7 \times 10^{-9}$ | 14.2 | 2570 | 10.8 |
| C | $5.6 \times 10^{-9}$ | 8.6 | 2756 | 11.7 |
| D | $5.7 \times 10^{-9}$ | 8.9 | 2505 | 10.5 |
| E | $6.0 \times 10^{-9}$ | 9.4 | 2653 | 11.2 |
| F | $8.4 \times 10^{-9}$ | 13.6 | 3406 | 14.8 |
| G | $6.5 \times 10^{-9}$ | 10.2 | 2205 | 9.1 |
| H | $6.0 \times 10^{-9}$ | 9.4 | 2555 | 10.7 |
| I | $4.2 \times 10^{-9}$ | 6.4 | 2101 | 8.7 |

$^+$Determined by radioreceptor assay from plasma originally containing $7 \times 10^{-8}$M (±) - propranolol.
*In 50 μl dialysate from plasma originally containing $2.6 \times 10^4$ cpm $^3$H-propranolol per 50 μl and $7 \times 10^{-8}$ M (±) - propranolol.

Data are presented as mean values of triplicate runs which varied less than 5%.

As can be seen from the table, the radioreceptor assay method described herein is accurate in measuring levels of free propranolol in the blood.

I claim:

1. The method of determining the concentration of free β-adrenergic blocking drugs and any active metabolites thereof in a body fluid containing same comprising (a) dialyzing the body fluid (b) mixing together β-adrenergic receptor material, radioactive β-adrenergic receptor binder and the dialyzed body fluid, and measuring the amount of the radioactive β-adrenergic binder on the β-adrenergic receptor material and (c) mixing together a concentration of a standard amount of non-radioactive β-adrenergic receptor binder, β-adrenergic receptor material and radioactive β-adrenergic receptor binder and measuring the amount of radioactive β-adrenergic receptor binder on the β-adrenergic receptor material.

2. The method of claim 1 in which the material, binder, and dialyzed body fluid are permitted to remain together a time sufficient to produce sufficient binding of the binder, drugs and any active metabolites thereof in the body fluid to said receptor material prior to making the measurement.

3. The method of claim 1 in which the material, binder and dialyzed body fluid are combined in the presence of sufficient buffer to produce a pH of about 6 to 9.

4. The method of claim 1 in which unbound binder and dialyzed body fluid are removed as part of the measurement.

5. The method of claim 1, 2, 3 or 4 in which the dialyzed body fluid is blood plasma or blood serum.

6. The method of claim 1 in which measuring of the amount of radioactive receptor binder on the receptor material is determined in a gamma detector or scintillation counter based upon the nature of the radionuclide portion of the radioactive binder.

7. The method of claim 1 or 6 in which the concentration of drug and active metabolite is determined by reference to a standard curve representing percent inhibition of radioactive receptor binder vs. non-radioactive receptor binder.

8. The method of claim 1 in which the concentration of body fluid is less than about 10%.

9. The method of claim 1 or 8 in which the dialyzed body fluid is blood plasma or blood serum.

10. The method of claim 1 or 8 in which the amount of dialyzed body fluid in the mixture containing same is greater than one microliter.

11. The method of claim 1 in which the unbound drug, unbound radioactive binder and dialyzed body fluid are removed in determining the percent inhibition of binding.

12. The method of claim 1 in which the radioactive receptor binder is a radioactive labeled drug selected from the group consisting of:
 1. propranolol
 2. practalol
 3. pindalol
 4. alprenolol
 5. sotalol
 6. butoxamine 13. The method of claim 1 in which the receptor material is brain tissue.

14. The method of claim 1 in which (c) is repeated a sufficient number of times while varying concentrations of the non-radioactive binder to provide information for generating a standard curve.

15. The method of claim 9 in which the amount of dialyzed body fluid in the mixture containing same is greater than one microliter.

16. The method of claim 9 in which the unbound drug, unbound radioactive binder and dialyzed body fluid are removed in determining the percent inhibition of binding.

17. The method of claim 9 in which the radioactive receptor binder is a radioactive labeled drug selected from the group consisting of:
 1. propranolol
 2. practalol
 3. pindalol
 4. alprenolol
 5. sotalol
 6. butoxamine 18. The method of claim 9 in which the receptor material is brain tissue.

19. The method of claim 9 in which (c) is repeated a sufficient number of times while varying concentrations of the non-radioactive binder to provide information for generating a standard curve.

* * * * *